United States Patent
Carroll et al.

(10) Patent No.: US 6,488,691 B1
(45) Date of Patent: Dec. 3, 2002

(54) LAPARASCOPIC INCISION CLOSURE DEVICE

(76) Inventors: Brendan J. Carroll, 2278 Betty La., Beverly Hills, CA (US) 90210; Jeffrey S. Kadan, 215 Via Linda Vista, Redondo Beach, CA (US) 90277; Frederick Gotha, 957 Coronado Dr., Arcadia, CA (US) 91006; Gregory M. Miles, 7055 Divot Dr., La Verne, CA (US) 91750

( * ) Notice: Subject to any disclaimer, the term of this patent is extended or adjusted under 35 U.S.C. 154(b) by 0 days.

(21) Appl. No.: 09/564,771

(22) Filed: May 3, 2000

Related U.S. Application Data

(63) Continuation-in-part of application No. 09/103,765, filed on Jun. 24, 1998.

(51) Int. Cl.[7] ............................................. A61B 17/04
(52) U.S. Cl. ...................................................... 606/148
(58) Field of Search ................................ 606/148, 144, 606/139, 232

(56) References Cited

U.S. PATENT DOCUMENTS 3,185,367 A    5/1965   Rieger et al.
D223,138 S     3/1972   Mulholland et al.

(List continued on next page.)

Primary Examiner—Michael J. Milano
Assistant Examiner—Daniel Jacob Davis
(74) Attorney, Agent, or Firm—Frederick Gotha

(57) ABSTRACT

A laparascopic incision closure device comprised of an ejector housing having a handpiece trigger that is activated by compression and is biased to return to an initial position. The handpiece is so carried by the ejector housing that compression and retraction of the handpiece sequentially advances a flexible wire push-rod to eject a T-bar suture and retracts the flexible wire push-rod to index a ratchet which feeds the T-bar portion of a T-bar suture into the longitudinal bore of a needle carried by the ejector housing. The strand portion of the T-bar suture trails the T-bar portion through the longitudinal bore. Multiple T-bar sutures are axially spaced and detachably carried on a suture spline by spline mount tabs connected to the T-bar portion of the T-bar sutures and are stored in the interior of the ejector housing for quick and easy placement through fascia on opposite sides of a wound. In the preferred embodiment the device is constructed of a disposable plastic material with sutures being formed of an absorbable material.

12 Claims, 20 Drawing Sheets

U.S. PATENT DOCUMENTS

| | | | | |
|---|---|---|---|---|
| 3,650,451 A | | 3/1972 | Weiland et al. | |
| 3,650,452 A | | 3/1972 | Finke | |
| 3,901,428 A | | 8/1975 | Grass | |
| 3,918,143 A | | 11/1975 | Grushan | |
| 3,931,667 A | * | 1/1976 | Merser et al. | 24/150 |
| 3,971,497 A | | 7/1976 | Hamisch, Sr. | |
| 3,971,498 A | | 7/1976 | Bussard | |
| 5,973,710 A | | 8/1976 | Strausburg | |
| 4,040,555 A | | 8/1977 | Jenkins | |
| 4,049,174 A | | 9/1977 | Hamisch, Sr. | |
| 4,049,175 A | | 9/1977 | Hamisch | |
| 4,049,176 A | | 9/1977 | Jenkins | |
| 4,049,177 A | | 9/1977 | Bussard | |
| 4,049,178 A | | 9/1977 | Strausburg | |
| 4,425,394 A | | 1/1984 | Jenkins | |
| 4,610,384 A | | 9/1986 | Duchin | |
| 4,610,385 A | | 9/1986 | Duchin | |
| 4,634,036 A | | 1/1987 | Duchin | |
| 4,669,473 A | * | 6/1987 | Richards et al. | 606/215 |
| 4,671,442 A | | 6/1987 | Duchin | |
| 4,673,120 A | | 6/1987 | Strausburg | |
| 4,681,248 A | | 7/1987 | Duchin | |
| 4,682,721 A | | 7/1987 | Duchin | |
| 4,683,635 A | | 8/1987 | Duchin | |
| 4,690,317 A | | 9/1987 | Hamisch, Jr. et al. | |
| 4,696,422 A | | 9/1987 | Strausburg | |
| 4,706,362 A | | 11/1987 | Strausburg | |
| 4,711,369 A | | 12/1987 | Duchin | |
| 4,715,521 A | | 12/1987 | Strausburg | |
| 4,838,469 A | | 6/1989 | Strausburg | |
| 5,041,129 A | * | 8/1991 | Hayhurst et al. | 606/139 |
| 5,085,661 A | * | 2/1992 | Moss | 606/144 |
| 5,508,661 A | * | 2/1992 | Moss | 606/139 |
| 5,290,279 A | * | 3/1994 | Phillips | 606/144 |
| 5,480,961 A | * | 1/1996 | Jiang et al. | 528/220 |
| 5,507,754 A | * | 4/1996 | Green et al. | 606/139 |
| 5,741,278 A | * | 4/1998 | Stevens | 606/139 |
| 5,810,848 A | * | 9/1998 | Hayhurst | 606/139 |
| 4,785,987 A | | 11/1998 | Strausburg | |
| ,016,747 A1 | * | 8/2001 | Romano et al. | 606/148 |

* cited by examiner

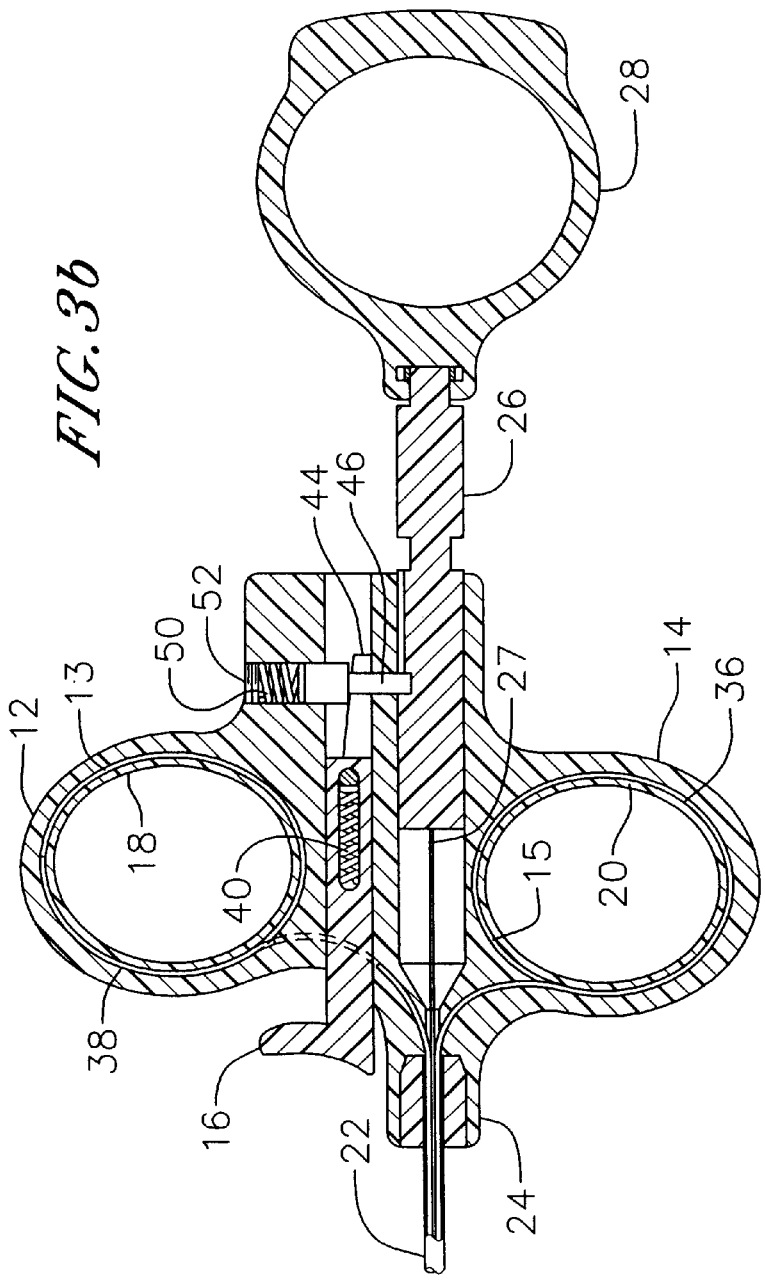

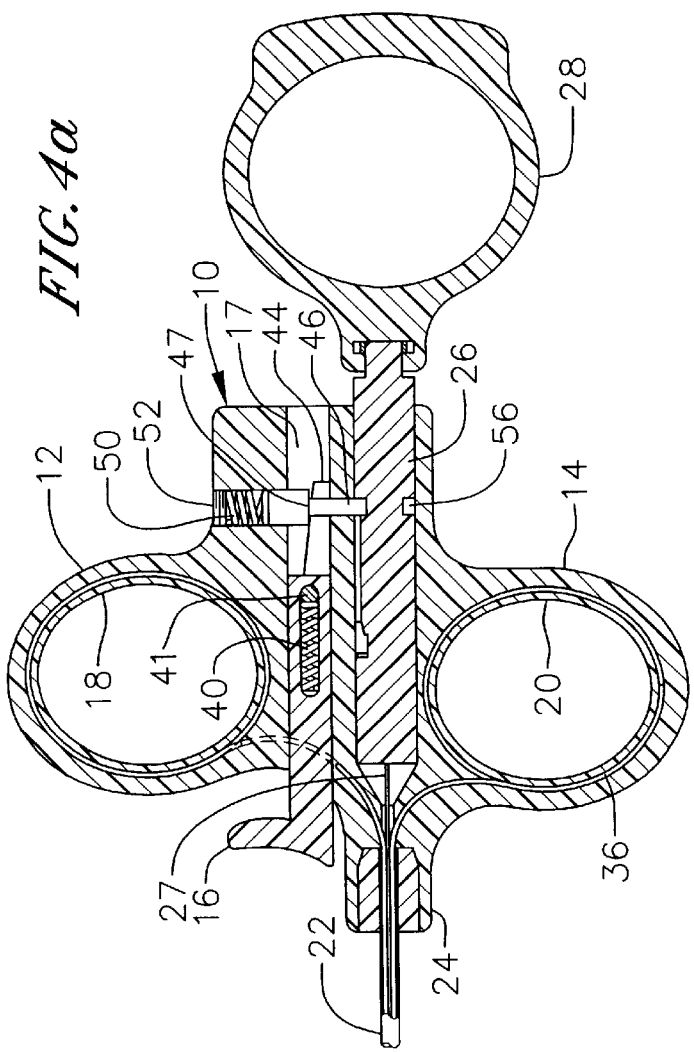
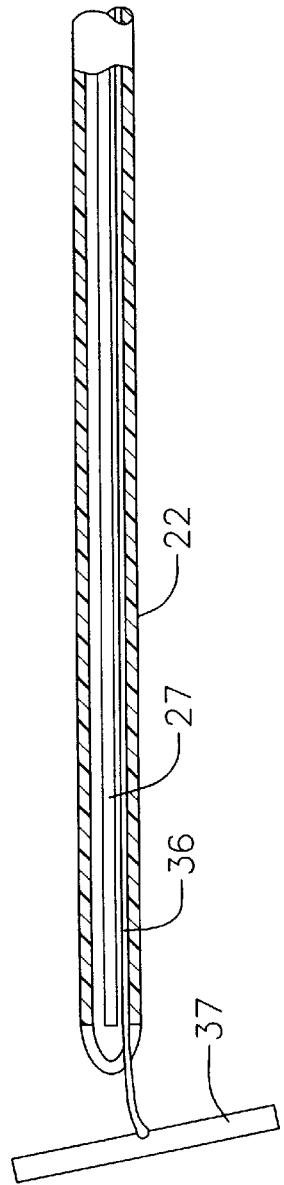
FIG. 4a
FIG. 4b

LAPARASCOPIC INCISION CLOSURE DEVICE

This is a Continuation-In-Part of U.S. application Ser. No. 09/103,765, filed Jun. 24, 1998.

BACKGROUND OF THE INVENTION

1. Field of the Invention

This invention relates to devices for placing sutures to close incisions and more particularly relates to a device and method to efficiently close small incisions used in laparascopic surgery.

2. Background Information

Laparascopic surgical procedures generally use small incisions some 5 to 16 millimeters in length for placement of a cannula and trocar used in laparascopic surgical procedures such as cholecystectomy, hemiorrhaphy, Nissen, hysterectomy, colectomy, etc. One method used to close such incisions is by simple surface skin or facial closures. However, a not infrequent problem with this and other methods is that the closures are not affective enough and lead to complications such as hernias and bowel strangulations.

Another method used to close such incisions is by a tedious procedure that requires a surgeon to laparascopically grasp a suture from a closure insertion device after placement through the abdominal wall. The closure insertion device is then withdrawn and then reinserted through the abdominal wall on the opposite side of the trocar site incision. The surgeon must then reinsert the needle into the closure insertion device and then withdraw it creating a loop around the trocar site incision. The tedious part of the process is the need to reinsert the suture into the closed insertion device which sometimes requires a surgeon to "work backwards" depending on the camera location.

Thus there is a need for a simple and preferably disposable device for closure of trocar site incisions used in laparascopic surgical procedures described above. A device that could quickly, efficiently and atraumatically insert sutures to close a laparascopic incision would be advantageous.

There is an existing device called a Brown/Mueller Fastener described in U.S. Pat. No. Re. 34,021 of Peter R. Mueller et al, that is designed to insert a T-bar fastener through the abdominal wall. This device has a needle with a slot in the end for receiving a metal T-bar with a single short suture extending through the slot along the outside of the needle. The needle with the loaded metal T-bar and short suture is then inserted through the abdominal wall. The metal T-bar and attached suture is then extruded from the needle allowing the metal T-bar to fasten the suture inside the abdomen. This device is currently used for securing a portion of an intestine to the abdominal wall for placement of feeding tubes. A disadvantage of this device is that it allows placement of only a single suture which must be securely held by the surgeon while the needle is piercing the abdomen.

It is therefore one object of the present invention to provide laparascopic insertion/closure device that can quickly and efficiently place multiple T-bar sutures on opposite sides of a trocar site incision to close the wound.

Another object of the present invention is to provide a laparascopic incision closure device that can store multiple T-bar sutures inside a housing.

Still another object of the present invention is to provide a laparascopic incision closure device having an ejection mechanism for firing and ejecting one T-bar suture at a time. dr

BRIEF DESCRIPTION OF THE INVENTION

The purpose of the present invention is to provide a laparascopic incision closure device and method for quickly and efficiently placing multiple T-bar sutures on opposite sides of a trocar site incision to close defects left by the incision.

The laparascopic incision closure device is particularly designed and adapted to close small incision, used in laparascopic surgery on such as cholecystectomy, herniorrhaphy, Nissen, Hysterectomy, colectomy, and the like. These incisions are generally 5 to 16 millimeters in length and allow instruments to be passed through the abdominal wall through a cannula. The defect left by these incision must be closed to prevent development of complications such as hernia and bowel strangulation.

In the preferred embodiment of the laparascopic incision closure device of this invention, the device consists of a housing having a handpiece that is biased by a spring member toward an unactivated position. The handpiece carries a drive rack that rotates a pinion in one direction when the handpiece is compressed and in the other direction when the handpiece is released and returns toward the unactivated position. A needle having a longitudinal axis and a longitudinal bore forming a bounded passageway through the needle, is carried by the housing. To feed T-bar sutures into the longitudinal bore for ejection through the bore and out of the needle distal tip, a spline member having an axis of elongation spaced radially in relationship to the longitudinal axis of the longitudinal bore which extends through the needle, is moveably mounted to the housing; a plurality of axially spaced T-bar sutures are detachably carried by the spline member by respective mounting tabs extending from each T-bar portion. To feed a T-bar portion into the longitudinal bore, a ratchet mechanism activated by sufficient return movement of the handpiece engages a mounting tab and indexes the suture spline to feed a T-bar portion into the longitudinal bore. By compressing the handpiece from its unactivated position, a wire push-rod member engages the T-bar portion so as to advance it and its trailing suture portion through the longitudinal bore and to sever the T-bar portion mounting tab from the spline member. When the handpiece reaches its limit of travel position, the T-bar portion is ejected through the radial distal opening in the needle. With the handpiece held in the limit position, the needle is withdrawn through the tissue and the trailing suture strand portion passes through the radial distal opening of the needle. By releasing the handpiece, the wire push-rod is retracted, the ratchet indexed, and the spline member is advanced to feed another T-bar portion into the longitudinal bore.

In another embodiment, the laparascopic incision closure device is comprised of an ejector housing having finger gripping holes and a needle extending from the end of the housing. The needle is preferably about 18 millimeters. Multiple T-bar sutures are stored in the needle with the suture extending up the needle and stored inside the ejector housing. In one embodiment the sutures extend into the housing and wrap around inside the rings forming finger gripping holes.

A plunger extending through the needle ejects T-bar sutures one at a time by activation of a trigger that fires and releases a plunger shaft pushed forward by the thumb placed in a thumb ring on the end of the shaft. When loaded the plunger shaft position is locked by a spring operated pin. The pin engages a slot in the side of the plunger shaft.

The trigger is preferably mounted in the housing below the rings forming the finger handles. The trigger has a tapered end forming a cam that engages a shoulder on the locking trigger pin to dislodge the pin from the plunger shaft allowing the plunger shaft to move forward pushing the plunger along the needle to eject a T-bar suture. A second socket along the plunger shaft locks the trigger with the plunger in position for ejecting another T-bar suture from the needle.

To place a second T-bar suture the locking pin is again released from the second socket by operation of the trigger allowing the plunger shaft to be retracted by the thumb in the thumb ring. This positions a second T-bar suture for ejection from the needle. As the plunger shaft is retracted the locking plunger and pin slide along a groove in the trigger shaft and again lock in a first socket ready for repeat operation.

In a less preferred embodiment the trigger is a rotatable lever or button above the finger rings in the ejector housing having a pointed end engages detents in the plunger shaft. The trigger is pivotally mounted on a pin and has a tip that is biased into engagement with detents on the plunger shaft by a spring. To operate the device the trigger button is pushed or tilted toward the ejector housing releasing the tip from a plunger shaft detent allowing the plunger shaft to advance advancing the plunger to eject a T-bar suture. A second detent in the trigger shaft re-engages the trigger when the T-bar suture is ejected. To place another suture the trigger button is again operated allowing the plunger shaft to be further advanced by the thumb ring positioning the suture plunger in the needle for ejection of a second T-bar suture.

The laparascopic incision closure device is preferably constructed of a disposable plastic material with multiple T-bar sutures carried on a suture spline that has spline mount tabs detachably connecting the T-bar portion of the T-bar sutures to the suture spline. A suture strand portion extends from the T-Bar portion and has a free end that trails the T-bar portion where the T-Bar suture is advanced through a longitudinal bore in the needle.

Preferably the sutures are placed with a cannula in place in a laparascopic incision. The sutures are also preferably made of an absorbable material such as an "O-Vicryl" suture attached to an absorbable T-bar made of material similar to that used in "Absalock Clips" such as polydioxone. The T-bar sutures are placed on either side of a trocar incision under direct visualization. Preferably, the laparascopic incision closure device needle is inserted through the fascia on one side of the wound with the cannula still in place. The needle is then withdrawn leaving the T-bar suture in place through the fascia. The needle is then inserted through the fascia of the opposite side of the wound and a second T-bar suture ejected. With the cannula removed the sutures then can be tied over the fascia defect externally. Thus all surgeon needs to do is insert T-bar sutures through the fascia on either side of the cannula in the trocar site then tie the two sutures over the defect. The closure is very simple and cost effective.

The above and other novel features of the invention will be more fully understood from the following detailed description and the accompanying drawings, in which:

BRIEF DESCRIPTION OF THE DRAWINGS

FIG. 3b is a partial sectional view illustrating the laparascopic incision closure device in position for ejecting a second suture.

FIG. 3c illustrates the ejection of the first suture and the device in position for ejecting a second suture.

FIG. 4a is a sectional view illustrating operation of the device for ejecting a second suture.

FIG. 4b is a partial sectional view illustrating the ejection of the second suture.

FIG. 12(b) is a partial cross-sectional view taken along the line 12b—12b of FIG. 12a.

DETAILED DESCRIPTION OF THE INVENTION

Figure 1:
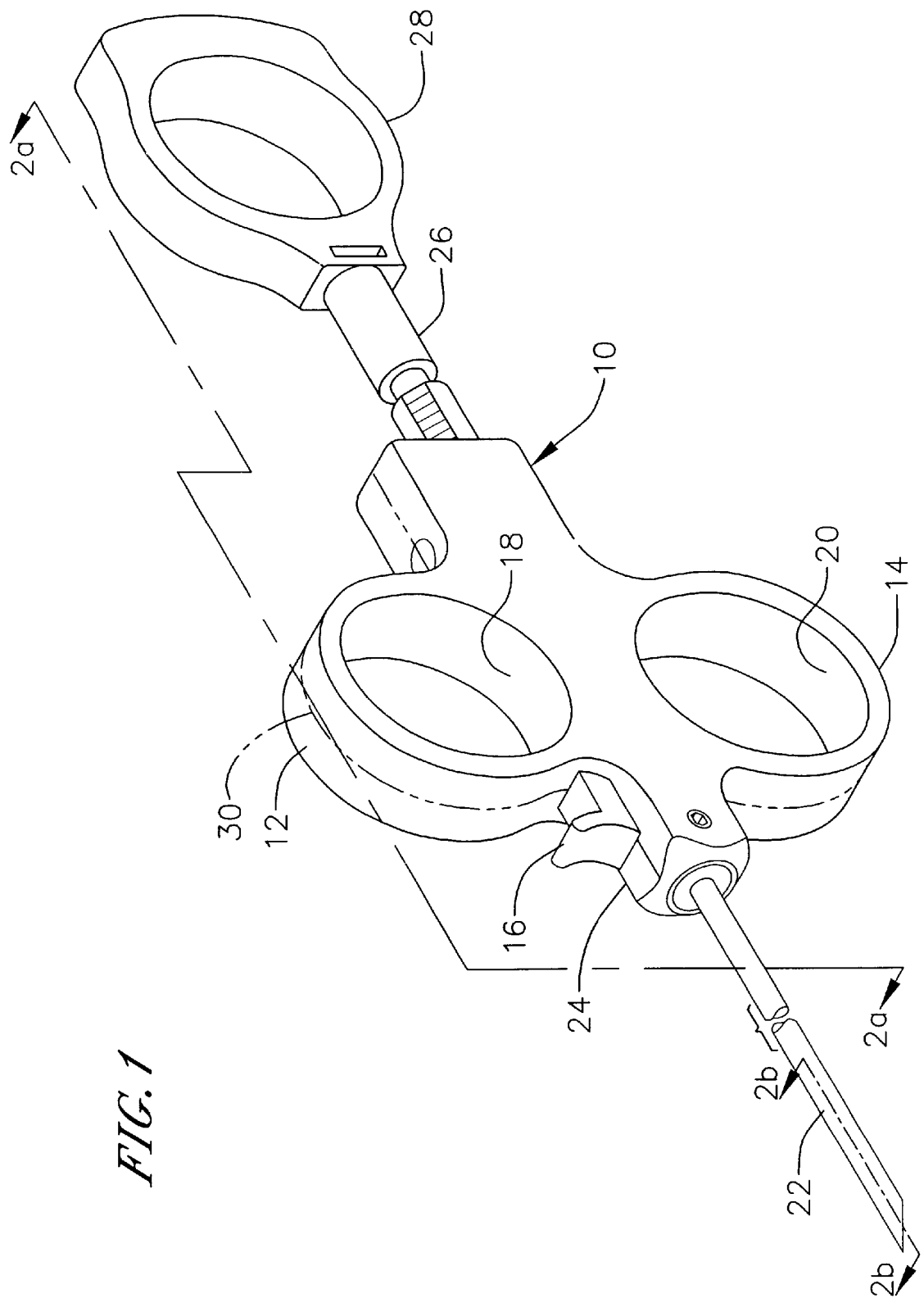
FIG. 1 is an isometric view of one embodiment of laparascopic incision closure device according to the invention.

A laparascopic incision closure device is shown in the isometric view of FIG. 1 and is comprised of an ejector housing 10 having finger rings 12 and 14 and a firing trigger 16. Finger rings 12 and 14 have finger holes 18 and 20 for use in operating the laparascopic incision closure device as will be described in greater detail hereinafter. A needle 22 is securely attached to an ejector housing extension 24 for ejecting a T-bar suture into the fascia of a wound as will also be described in greater detail hereinafter.

T-bar sutures are ejected by a plunger operated by plunger shaft 26 and thumb ring 28. Preferably ejector housing 10 is made of a disposable material such as a plastic in a clam shell construction indicated by dotted line 30.

Figure 2A:
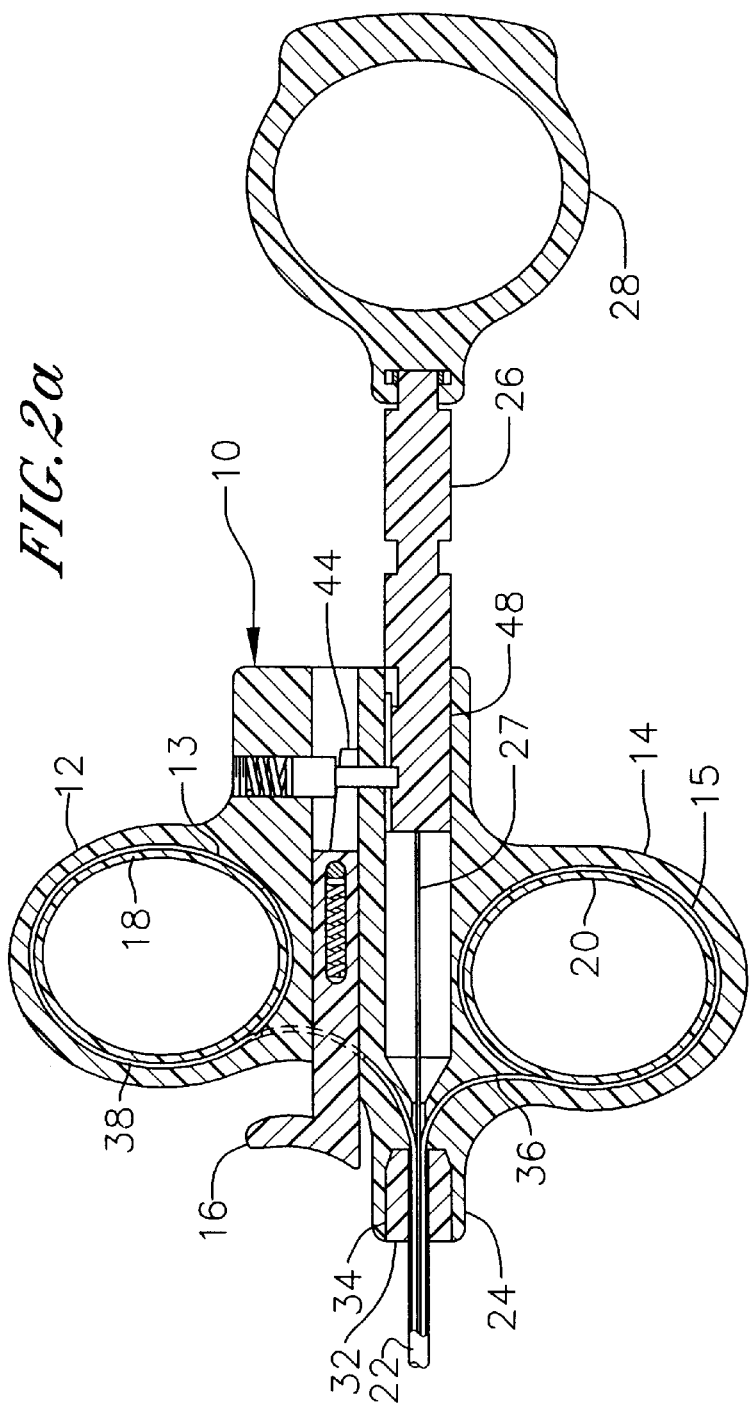
FIG. 2a is a sectional view taken at 2a of FIG. 1.
Figure 2B:
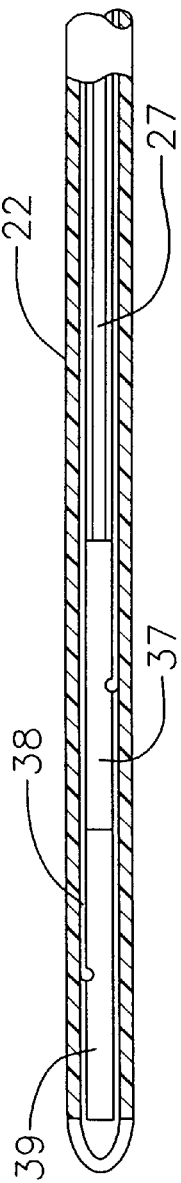
FIG. 2b is a sectional view taken at 2b of FIG. 1.

The internal construction of one embodiment of the laparascopic incision closure device is illustrated in FIGS. 2a and 2b. Needle 22 is securely attached to housing extension 24 by a boss 32 in a socket 34 securely clamped by Allen screw 36 (FIG. 1). Needle 22 holds multiple T-bar sutures 36 and 38 and plunger 27 attached to plunger shaft 26. Sutures 36 and 38 wind around circular cavities 13 and 15 in finger rings 12 and 14 and extend down needle 22. T-bar 39 on the end of suture 38 is positioned for ejection from the tip of needle 22 by the end of plunger 27. The device is illustrated with only two sutures in FIGS. 2a and 2b but a plurality of sutures can be provided if desired.

Figure 3A:
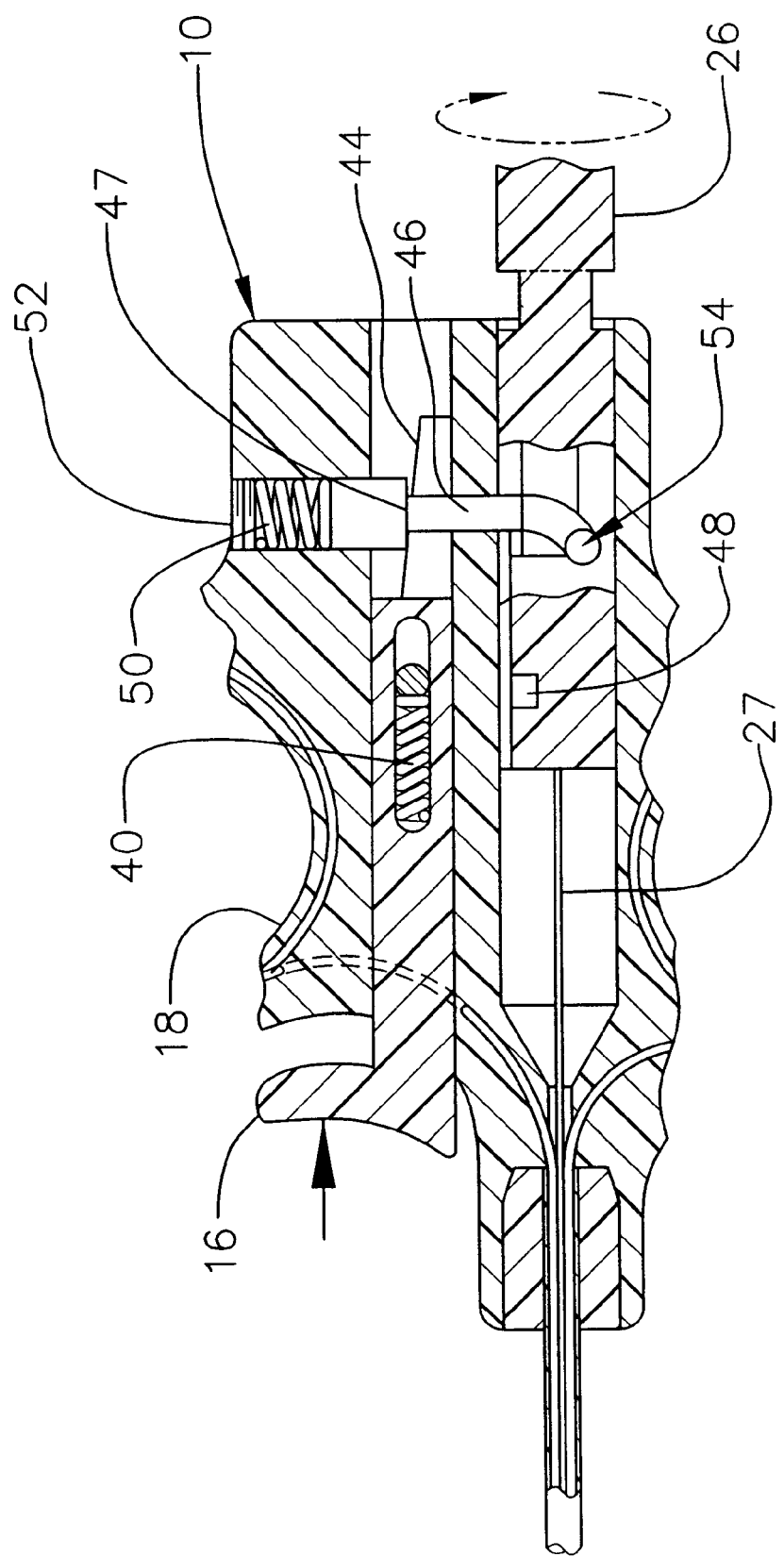
FIG. 3a is an enlarged partial sectional view illustrating the operation of the trigger firing mechanism.

Suture 38 with T-bar 39 is ejected from needle 22 by pressing downward on thumb ring 28 as will be described in greater detail hereinafter. The firing mechanism is comprised of a trigger 16 biased by a spring 40 in slot 42. Trigger 16 is a shaft 17 having fingers 44 forming a cam that engages shoulder 47 on trigger locking pin 46 biased into engagement with socket 48 in plunger shaft 26 by spring 50 as shown in greater detail in FIG. 3a. Trigger 16 is slidably mounted in bore 17 through ejector housing 10 and is held in position by pin 41 and biasing spring 40 in slot 42 in the trigger shaft.

The tapered cam surface on fingers 44 engage shoulder 47 on trigger locking pin 46. Trigger locking pin 46 is secured in ejector housing by Allen screw 52. When trigger 16 is pressed as indicated by the arrow the cam surface on fingers 44 engage shoulder 47 on locking pin 46 retracting it from socket 48 in trigger shaft 26 allowing plunger shaft 26 and plunger 27 to move forward until it reaches a stop position in a second socket 54. At this point the first T-bar 39 of T-bar suture 38 is ejected from the end of needle 22 as will be described in greater detail hereinafter. Preferably needle 22 is as an 18-millimeter bore 23 that will hold at least two T-bar sutures 36 and 38.

Release of a second suture from needle 22 is illustrated in the sectional views of FIG. 4a and 4b. To release the second suture trigger 16 is again operated allowing the cam surface on fingers 44 to engage shoulder 47 of locking pin 46 releasing it from socket 54 allowing trigger shaft 26 and plunger to advance ejecting a second T-bar 37 on suture 36 from needle 22. Locking pin stops at annulus 56 in plunger shaft 26.

Figure 5:
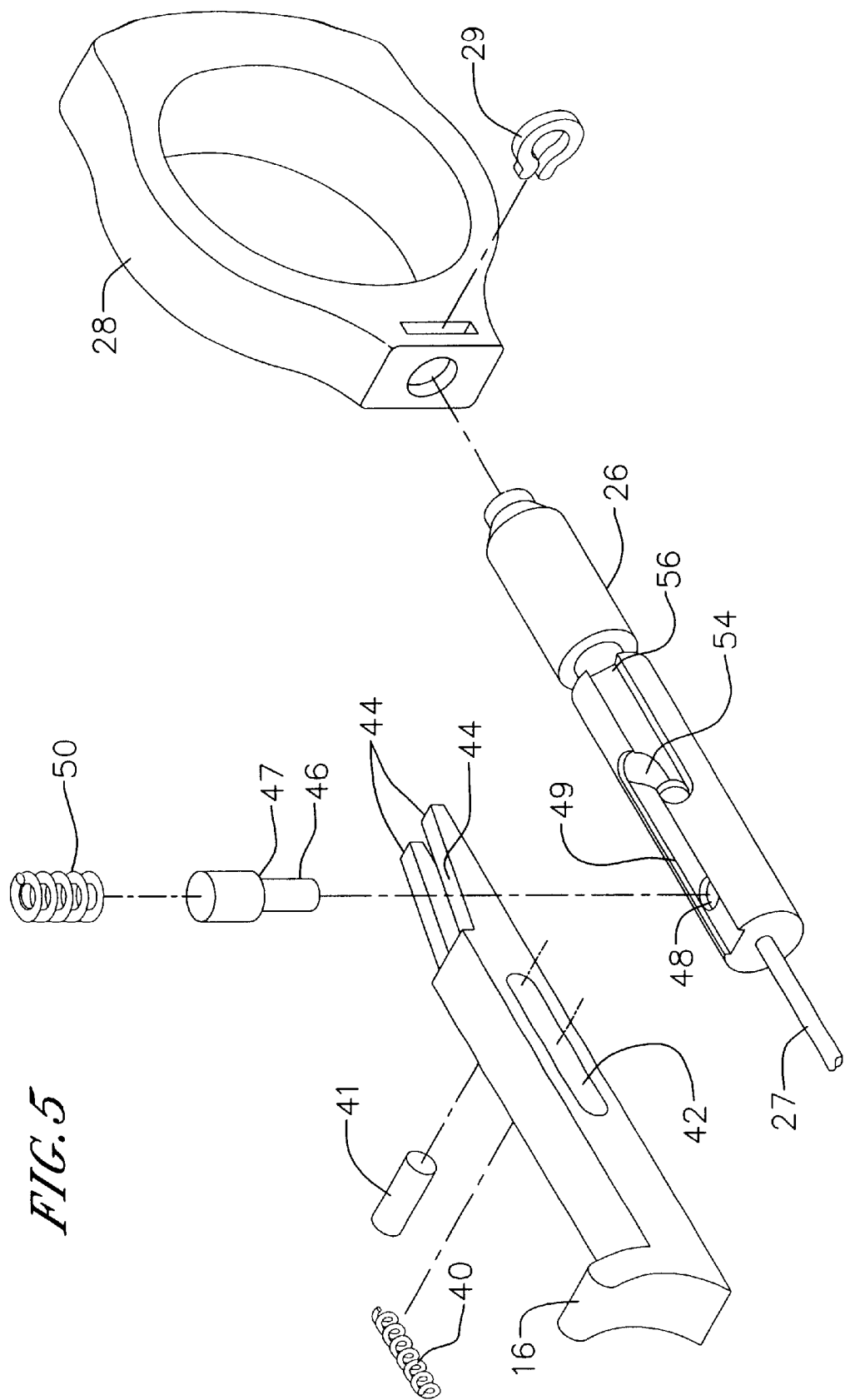
FIG. 5 is an exploded view illustrating the construction of the trigger mechanism and trigger shaft.

The details of the trigger mechanism are shown in the exploded view of FIG. 5. Trigger 16 is held in ejector housing 10 by pin 41 and spring 40 engaging slot 42. The end of trigger 16 has a pair of fingers 44 forming cam surface 45 that engages shoulder 47 on locking pin 46. Locking pin 46 locks the trigger shaft 26 by engaging socket 48 in axial groove 49. Release of locking pin 46 from socket 48 allows plunger shaft 26 to move forward until locking pin 46 engages socket 54. A further operation allows locking pin 46 to move along a continuation of slot 49 into annulus 56 to eject the second T-bar suture. Thumb ring 48 is attached to the end of trigger shaft by C-ring 29.

Figure 6A:
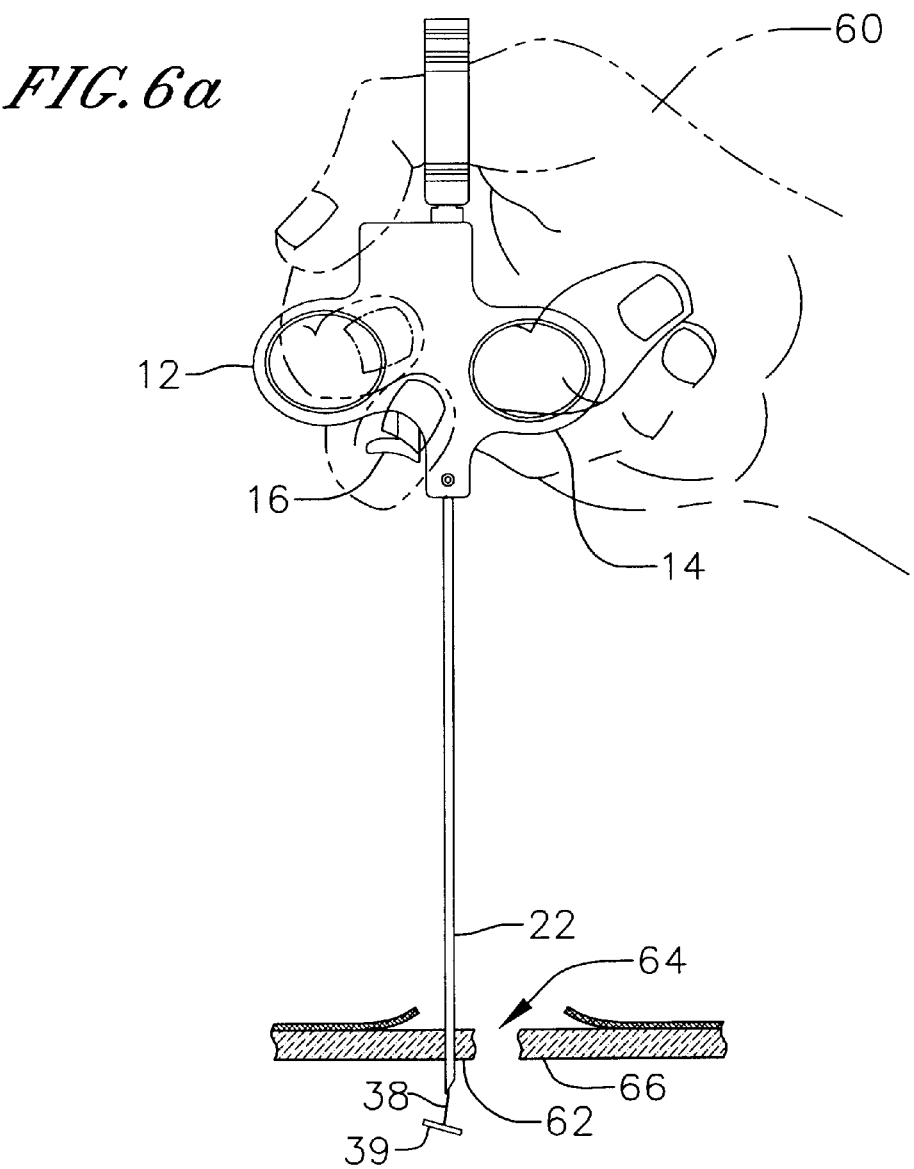
FIGS. 6a through 6c illustrate the operation of the laparascopic incision closure device.
Figure 6B:
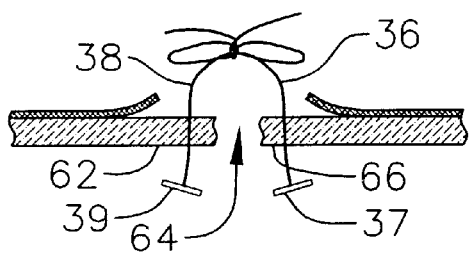
Figure 6C:
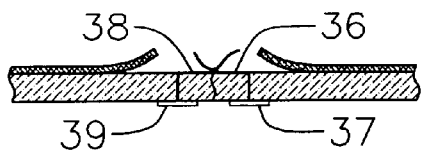

The operation of the device to release T-bar sutures on the opposite sides of a defect at a surgical site is illustrated in FIGS. 6a through 6c. The surgeon 60 grips the laparascopic incision closure device with the index and third fingers engaging finger rings 12 and 14 respectively and the middle finger positioned to activate trigger 16. With the laparascopic incision closure device in this position, needle 22 is inserted through fascia 62 on one side and incision 64. When needle 22 has passed completely through fascia 62, trigger 16 is fired allowing plunger shaft 26 and thumb ring 28 to move forward causing plunger 27 to eject T-bar 39 on suture 38. Withdrawal of needle 22 leaves suture 38 in place through fascia 62 with T-bar 39 against the abdominal wall.

This procedure is repeated in fascia 66 on the opposite side of incision 64 placing a second suture 37 with T-bar 38 through the abdominal wall. Preferably sutures 36 and 38 are an O-Vicryl sutures attached to absorbable T-bars 37 and 39 respectively made of a material similar to that used in "Absalock Clips" such as polydioxone. Optionally the T-bars could be made of titanium. With T-bar sutures 36 and 38 placed on opposite sides of the defects in incision 64, they are then tied over the fascial defect externally closing the wound as illustrated in FIG. 6c. Preferably sutures 36 and 38 are placed on opposite sides of the incision 64 while the cannula is still in place. After placement the cannula is then removed and the sutures 36 and 38 tied externally to close the wound.

Figure 7:
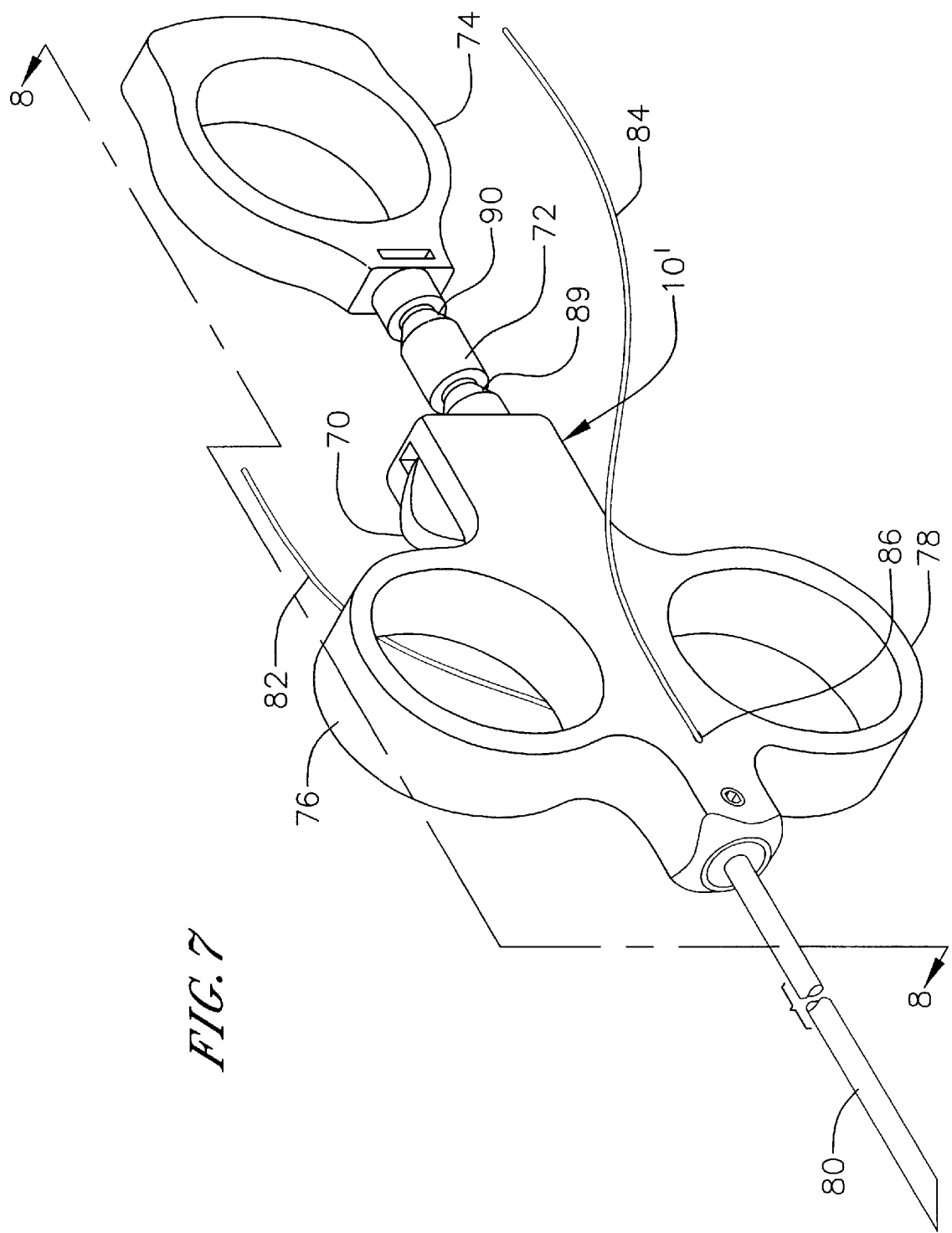
FIG. 7 is an isometric view of an alternate embodiment of the invention.

An optional embodiment of the laparascopic incision closure device is illustrated in FIG. 7. In this embodiment ejector housing 10' has a button trigger 70 engaging a plunger shaft 72 having thumb ring 74. Finger gripping rings 76 and 78 are provided as previously described. This design requires operation by thumb in ring 74 and the middle and ring finger in finger rings 76 and 78. Button triggers 70 would be operated by the index finger.

Needle 80 is attached to ejector housing 10' as described previously and has multiple T-bar sutures 82, 84 loaded in through ports 86, and 87 into needle 80. In this embodiment, T-bar sutures 82 and 84 are loaded through ports 86 and 87 on opposite sides of the ejector housing 10' rather than being in positioned internally as in the previous embodiment.

Figure 8:
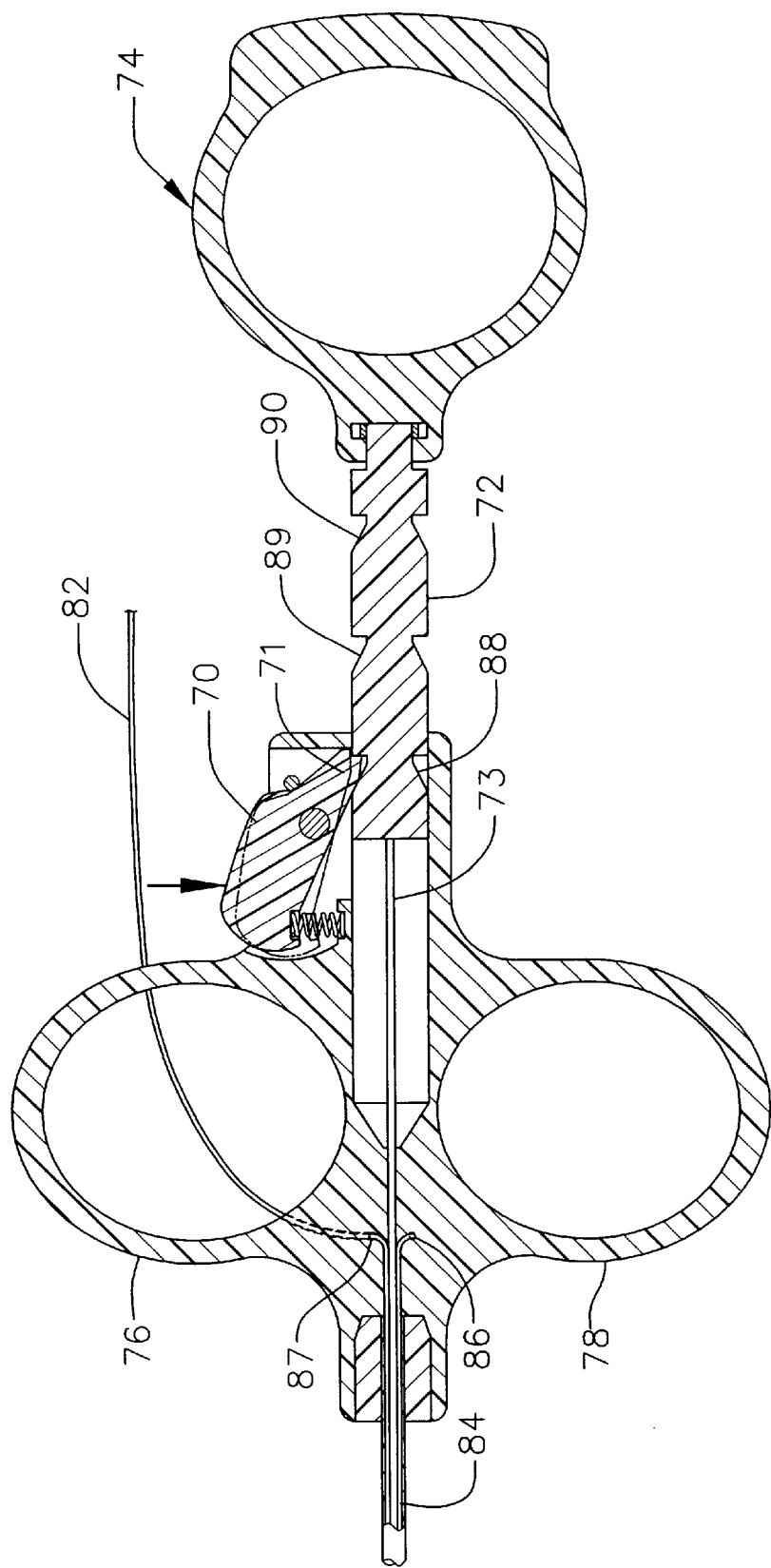
FIGS. 8, 9 and 10 are partial sectional views taken at 8—8 of FIG. 7 illustrate operation of the trigger mechanism of the second embodiment.
Figure 9:
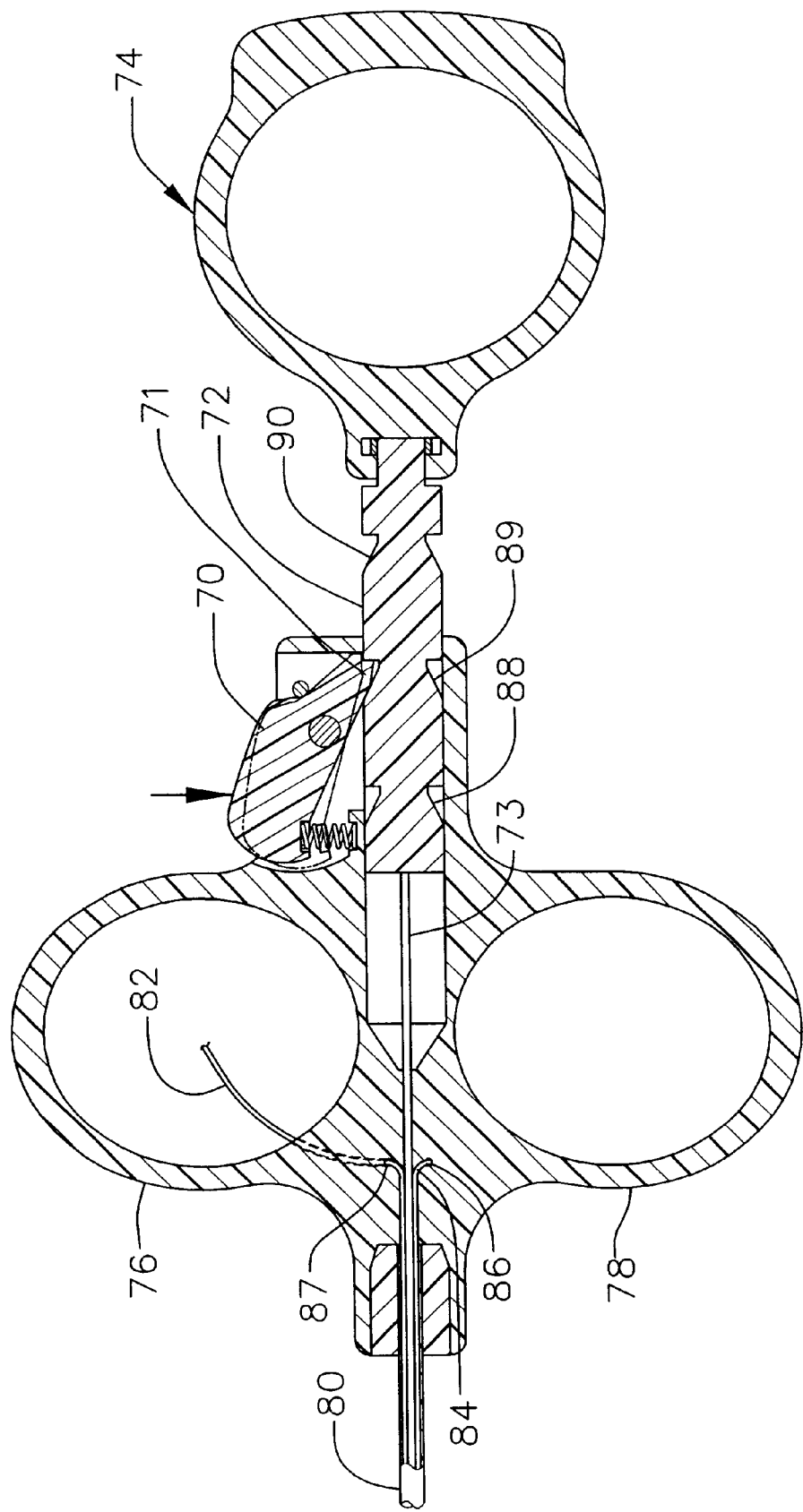
Figure 10:
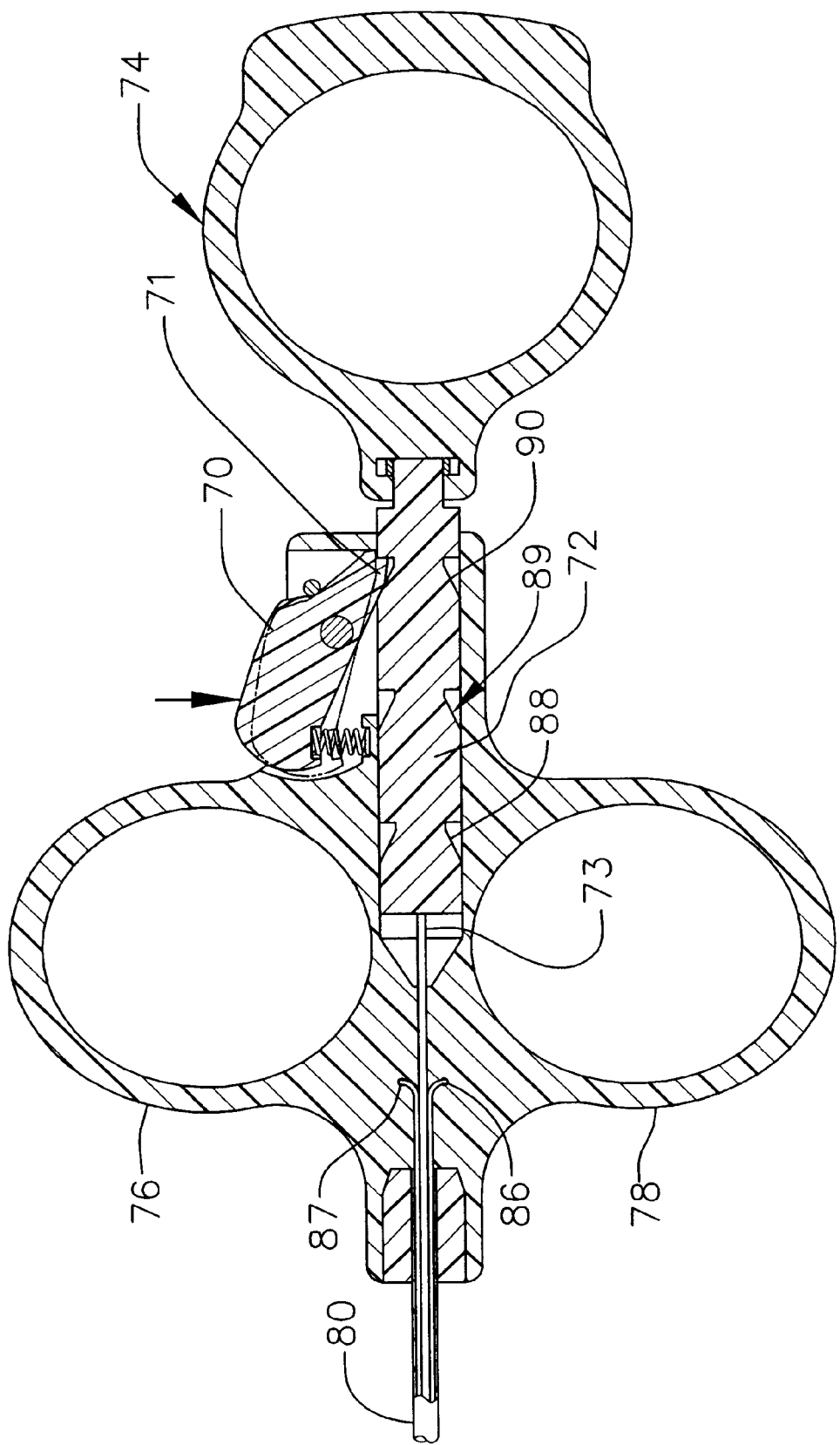

The operation of the button trigger laparascopic incision closure device is illustrated in FIGS. 8, 9 and 10. T-bar sutures 82 and 84 are positioned in needle 80 as shown in FIG. 2b with T-bars 37 and 39 positioned for ejection into the fascia of the wound. As shown in FIGS. 8 through 10, plunger shaft 72 is attached to plunger 73 which will eject T-bar sutures 82 and 84 from the end of needle 80. To operate this device the thumb is placed in thumb ring 74 and preferably the middle and ring fingers in finger holding rings 76 and 78. With the index finger trigger 70 is "fired" to dislodge trigger pin 71 from a first detent 88 in trigger shaft 70. This allows plunger shaft 72 and plunger 73 to move forward to eject a first T-bar suture through the fascia as illustrated in FIG. 6a.

Pin 71 on trigger 70 then engages second detend 89 in plunger shaft 72 stopping in this position as shown in FIG. 9. The laparascopic incision closure device is then removed from the fascia leaving the T-bar suture 82 in place. In this position the device is ready for placement of a second suture on the opposite side of an incision 64. Needle 80 is again inserted through fascia 66 on opposite side of incision 64 and trigger 70 fired again by an index finger dislodging trigger pin 71 from detend 89. This ejects a second T-bar suture 84 from the end of needle 80. Trigger pin 71 then stops in the third detent 90 in plunger shaft 72. The laparascopic incision closure device is then withdrawn leaving the second suture 84 in place in fascia 66. Sutures 82 and 84 are then tied closing wound 64.

Preferably the laparascopic incision closure device would be constructed of disposable material with sutures 82 and 84 of an absorbable material that dissolves over a period of time. Optionally the embodiment of FIGS. 8 and 9 could be constructed for re-use by re-loading T-bar sutures through ports 86 and 87 into needle 80. Reloading the laparascopic incision closure device is achieved by pressing button trigger 70 to remove plunger shaft 72 and plunger 73 from ejector housing 10'. Additional sutures can then be reloaded through ports 86 and 87 into needle 80 as desired.

Thus there has been disclosed a unique laparascopic incision closure device that can be used to place multiple sutures in defects at trocar site incisions. The device has an ejector housing and needle for storing multiple sutures that can be quickly and easily placed through the fascia on opposite sides of the defect in a trocar site incision. In one embodiment the laparascopic incision closure device has a convenient finger and thumb rings and a trigger for firing the device to eject a T-bar suture through the fascia adjacent to an incision. The needle is then withdrawn from the fascia leaving the T-bar suture in place and inserted through the fascia on the opposite side of the incision and fired again by operation of a trigger to place a second T-bar suture. The sutures are then tied off closing a wound. In the first embodiment of the trigger is an L-shaped lever positioned for easy operation by the middle finger of the hand to fire the device to eject each T-bar suture.

In another embodiment the trigger is a button trigger at the upper end of the ejector housing for operation by an index finger to sequentially eject T-bar sutures through the fascia on opposite sides of the wound. The device is simple in construction and provides multiple sutures for quick and easy placement and secure closure of laparascopic incisions to prevent complications such as hernia and bowel strangulations.

In the preferred embodiment shown in FIGS. 11 through 14(d), a trigger and firing mechanism is shown that permits spline 117 of T-bar sutures to be incrementally fed by a ratchet mechanism into the longitudinal bore of the needle and fired by compressing the handpiece of the trigger mechanism. Release of compression of the handpiece after firing will initiate withdrawal of flexible wire push-rod or plunger 106 followed by release of gear stop pawl 114 that permits advancement of pawl gear 116; this feeds the T-bar portion of the T-bar suture into the longitudinal bore of the needle. Plunger 106 is preferably made of flexible wire that can be wound on a carriage member such as a drum or pulley. During compression of the handpiece, drum 106 rotates in a direction that causes the wire push-rod to engage the T-bar portion of the suture which is then pushed through the longitudinal bore and ejected out of the distal tip of the needle. The strand portion of the T-bar suture trails the T-bar portion through the longitudinal bore and is in part ejected from the distal end of the needle along with the T-bar portion. By withdrawing the needle, the remainder of the suture strand passes through the longitudinal bore. The plunger is retracted by releasing the compressed handpiece which initiates the feeding of the succeeding T-bar suture portion into the longitudinal bore.

Figure 11:
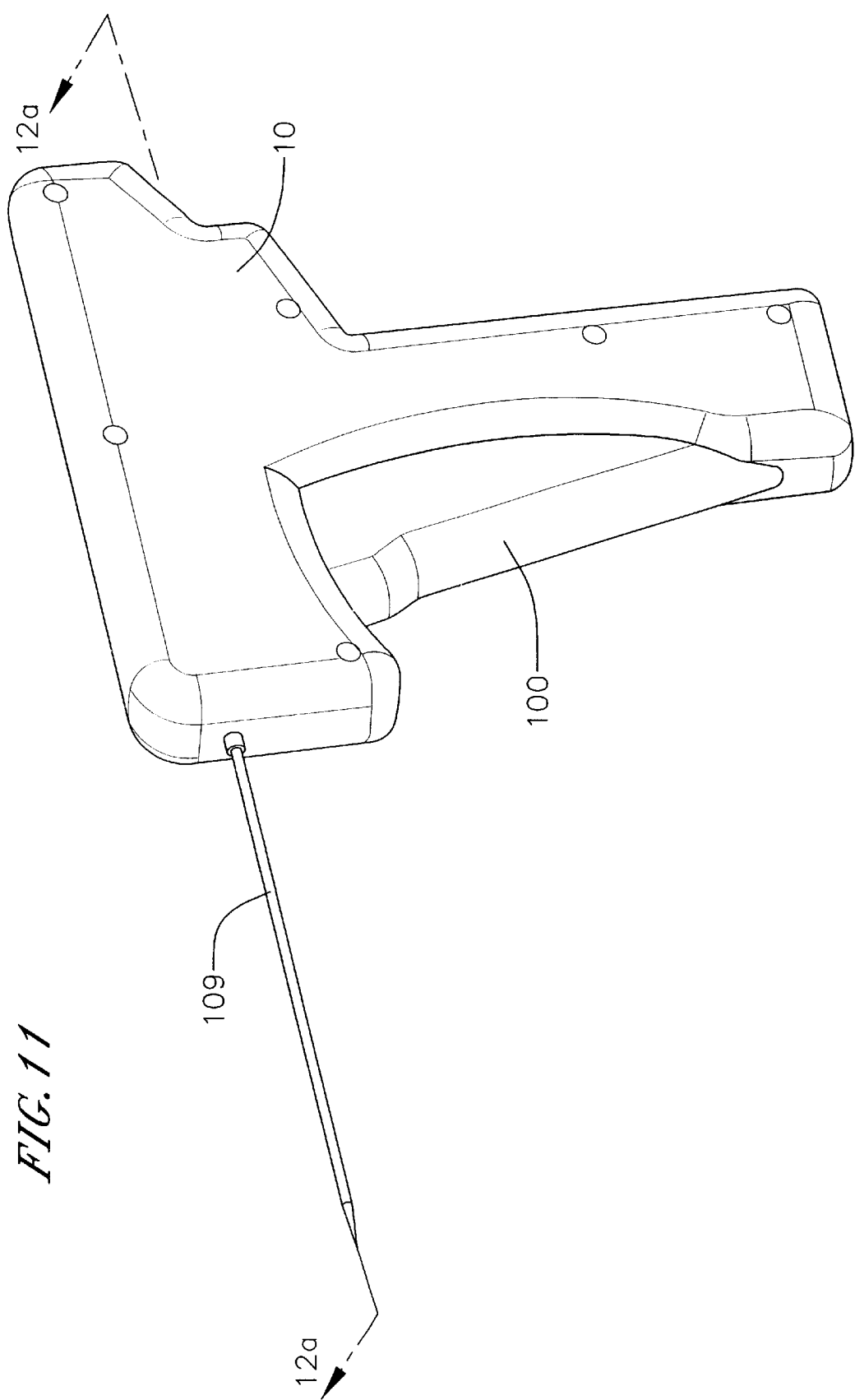
FIG. 11 is a perspective view of another embodiment of this invention.
Figure 12A:
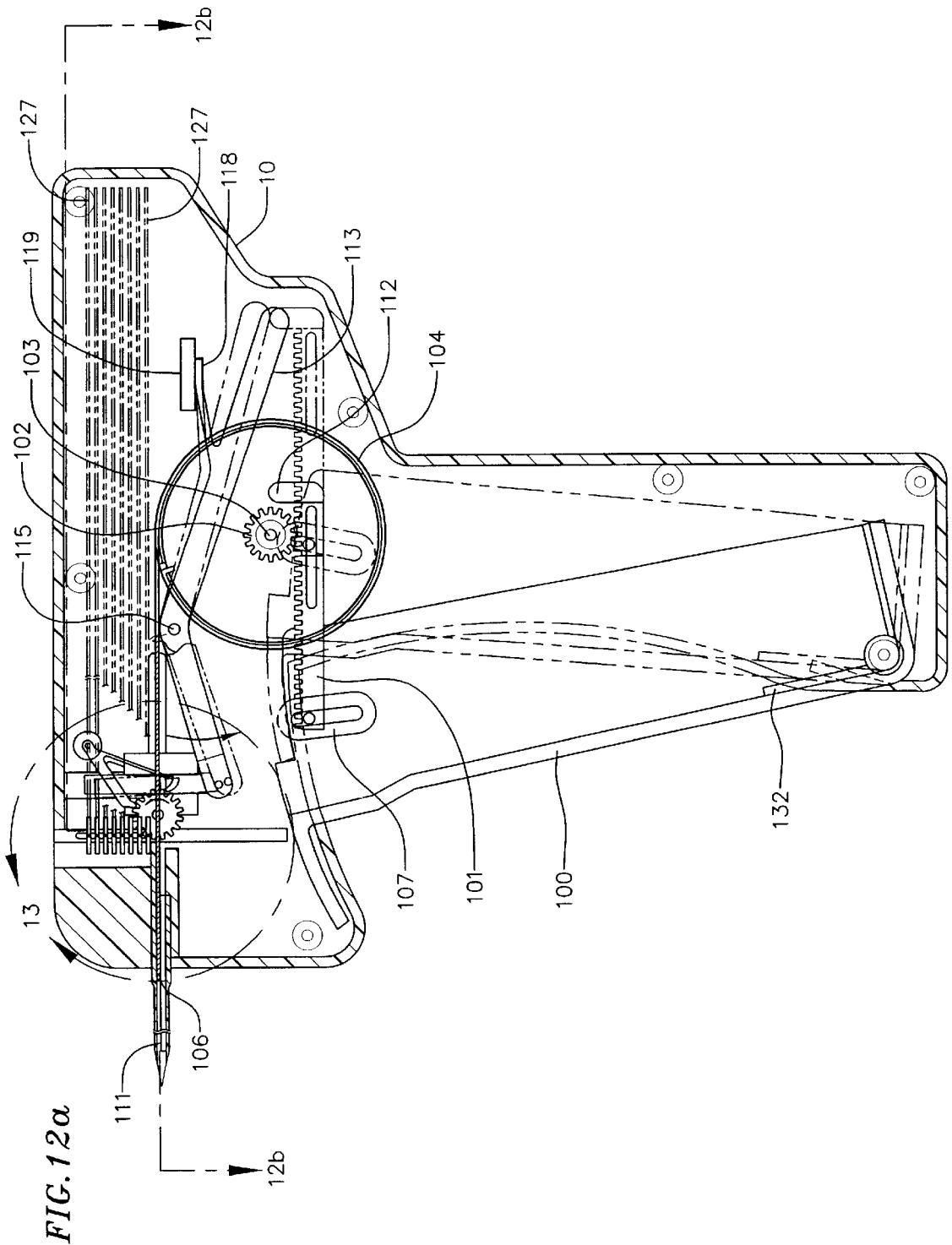
FIG. 12(a) is a partial cross-sectional view taken along the line 12a—12a of FIG. 11.
Figure 12B:
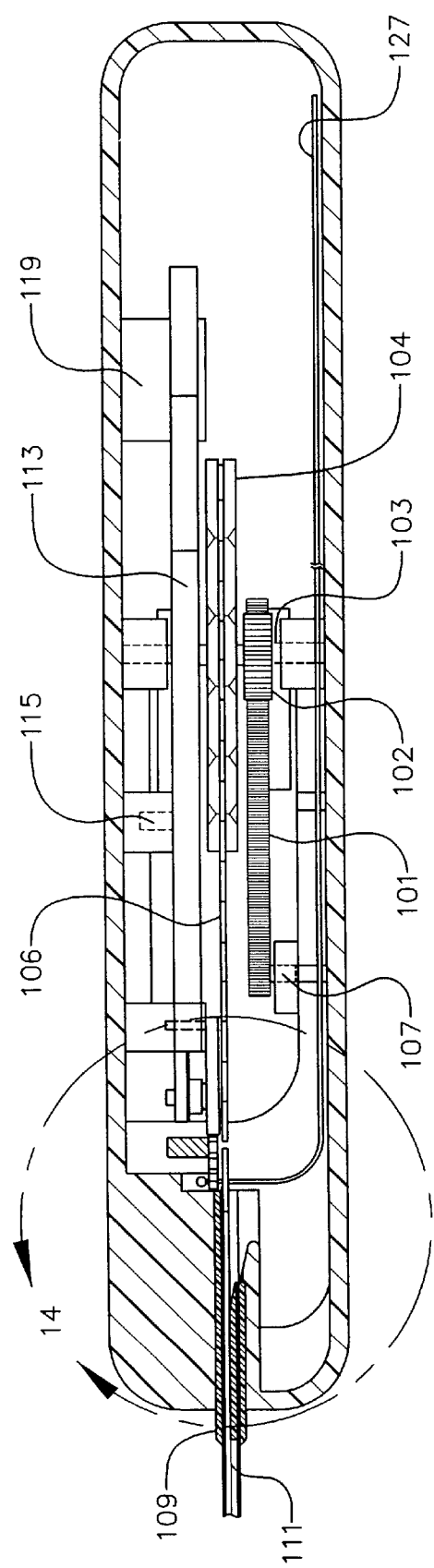

By referring to FIG. 12(a) which is a sectional view taken along the direction of line 12a—12a of FIG. 11, the preferred embodiment of this invention can be seen in greater detail. The handpiece 100 is shown in both the unactivated and activated positions. In the unactivated position, drive rack 101 is in engagement with pinion 102 which is keyed to the shaft 103 and carriage member or drum 104. By referring to FIG. 12(b), the wire push rod 106 can be seen in its retracted position on drum 104. Thus, when the handpiece 100 is compressed, drive rack 101, which is pin-yoked 107 to the handpiece, is displaced horizontally while in engagement with pinion 102, thereby rotating drum 104 and consequently advancing flexible wire push rod or plunger 106 through the longitudinal bore 108 of needle 109.

Figure 13A:
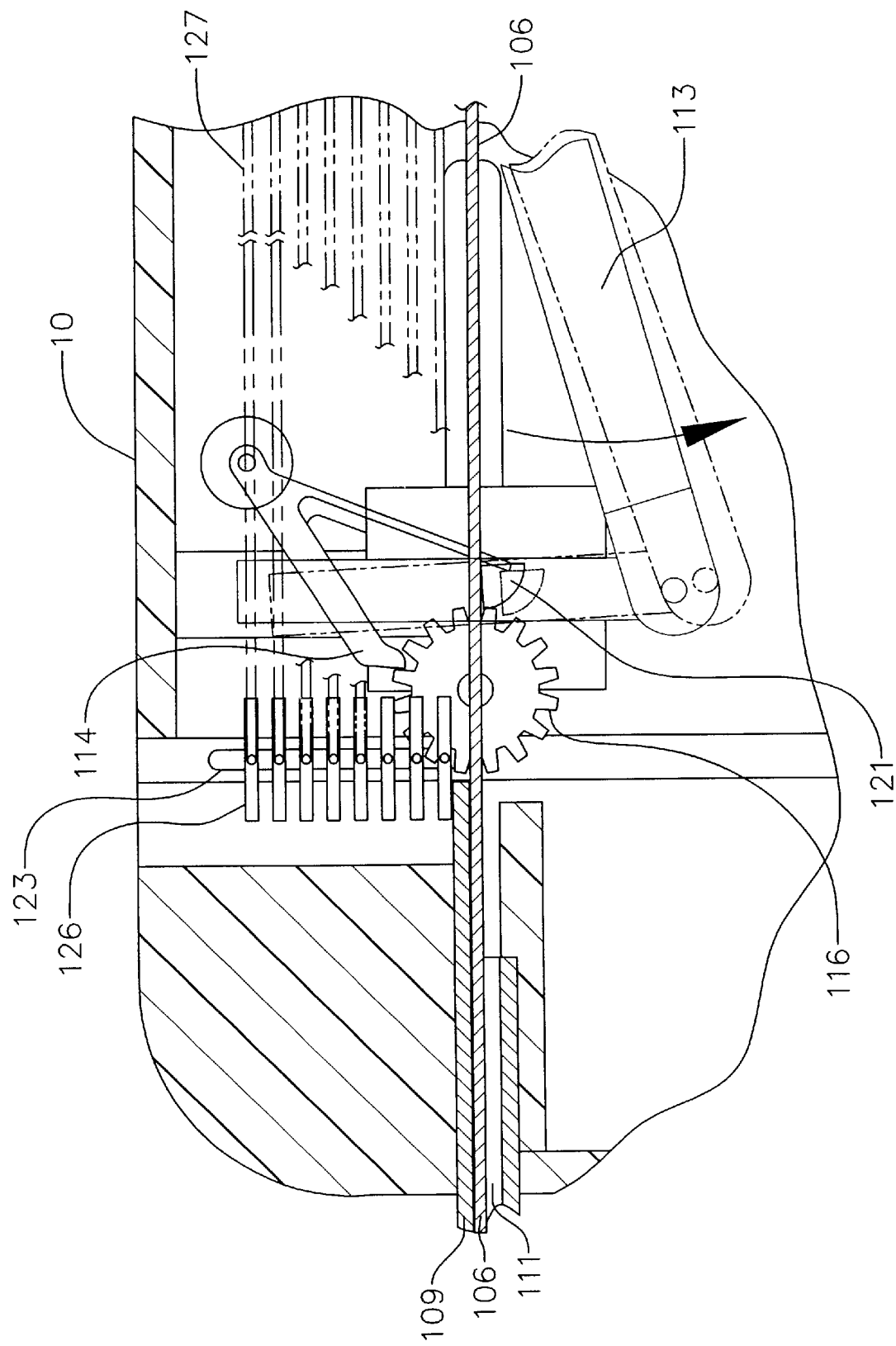
FIG. 13a is an enlarged view of the region identified by the Line 13 in FIG. 12a illustrating the trigger feeding mechanism in the unactivated to activated positions.
Figure 13B:
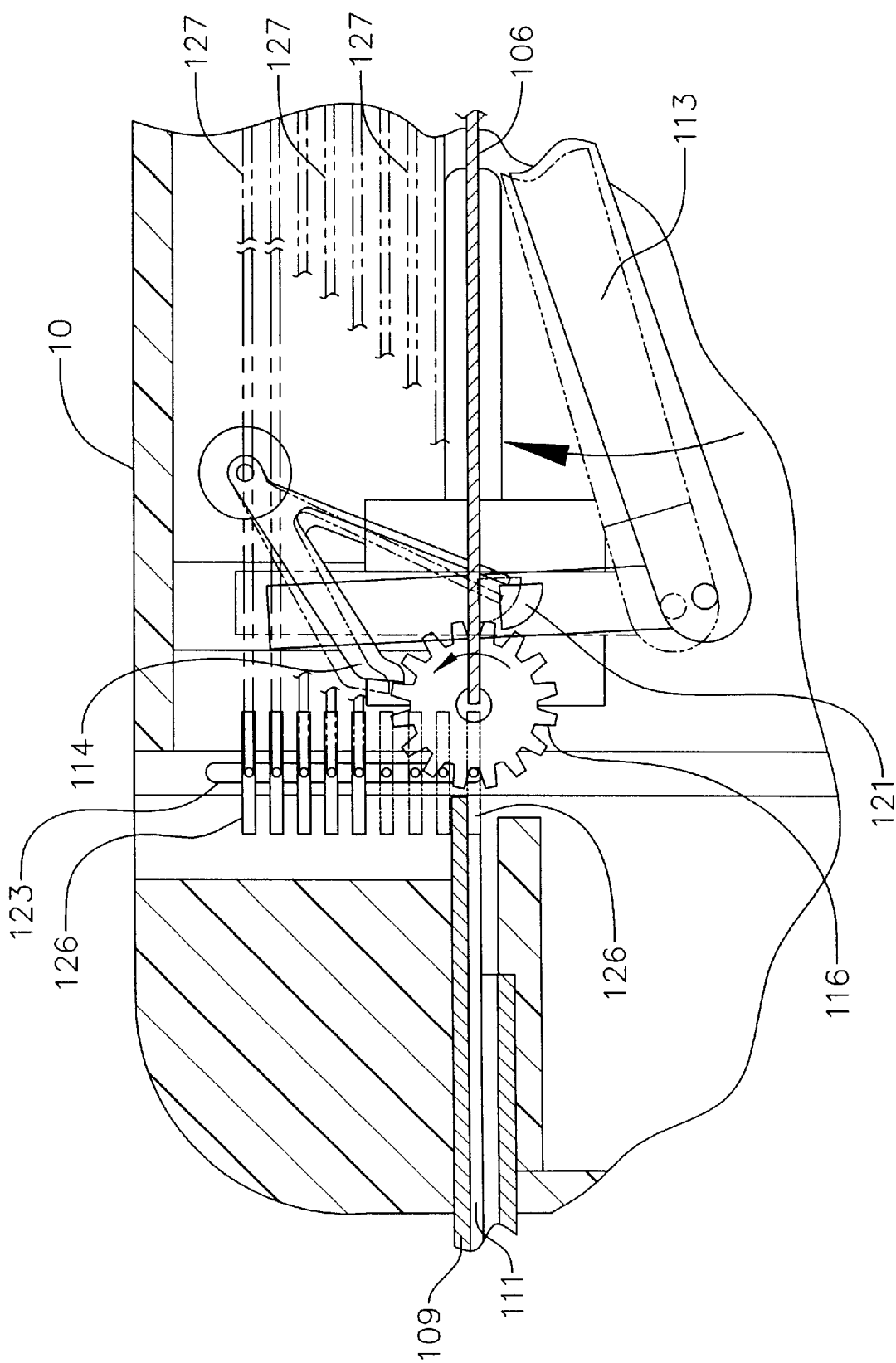
FIG. 13b is an enlarged view of the region identified by the Line 13 in FIG. 12a illustrating the trigger feeding mechanism in the activated to unactivated positions.

The sequential feeding mechanism of the T-bar sutures into the longitudinal bore 111 of needle 109 is illustrated in FIGS. 13a and 13b. As can be seen in 13(a), when the drive rack 101 is fully displaced horizontally by compression of the handpiece 100, boss 112 of drive rack 101 has caused rocker arm 113 to be rotated about pivot pin 115 to a first position which is the limit of counterclockwise travel of rocker-arm 113. Before reaching this limit and before boss 112 touches rocker arm 113, gear stop pawl 114 remains locked so as to prevent rotation of pawl gear 116. This prevents the advance of the T-bar suture spline 117 and consequently the feeding of a T-bar into longitudinal bore 111. After boss 112 engages rocker arm 113 and continues toward the first limit position, spring arm 118 is placed into compression by bearing against spring boss 119. As can be seen in FIG. 13b, when wire push-rod 106 is retracted sufficiently onto drum 104 by returning handpiece 100 towards its unactivated position, rocker-arm 113 will be urged by spring arm 118 to move in a clockwise direction to cause gear advance pawl 121 to engage pawl gear 116 which in turn engages spline mount tab 122 and advances suture spline 123 to feed the next succeeding T-bar suture into longitudinal bore 111. Handpiece 100 is biased by torsion spring 3 toward the unactivated position and each cycle of the handpiece results in a T-bar portion being ejected from the needle and the next succeeding T-bar suture carried on the suture spline 123 to be positioned in the longitudinal bore.

Figure 14A:
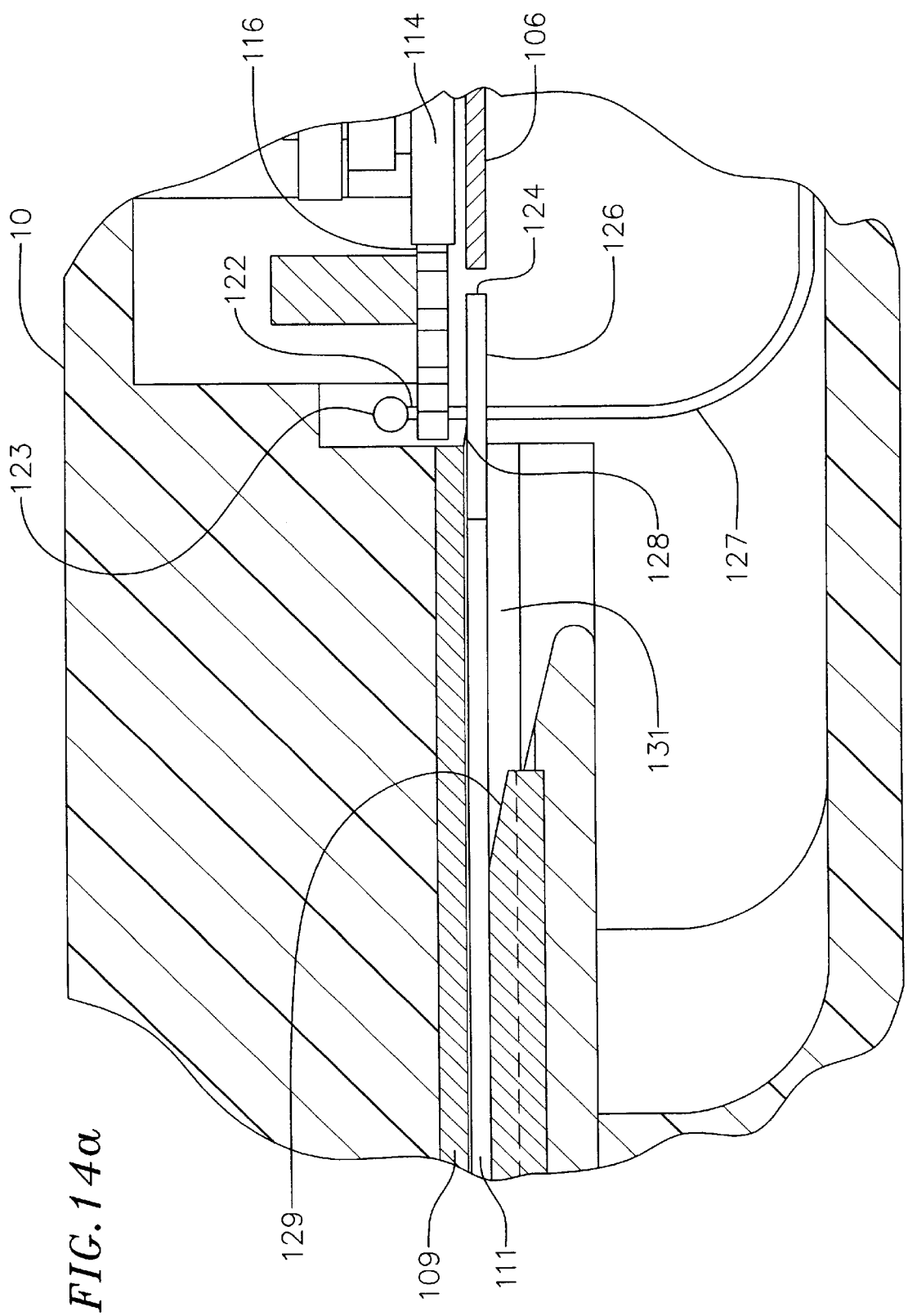
FIGS. 14a, 14b, 14c, and 14d are an enlarged view of the region identified by line 14 in FIG. 12b illustrating the sequence of feeding the T-bar suture into the needle.
Figure 14B:
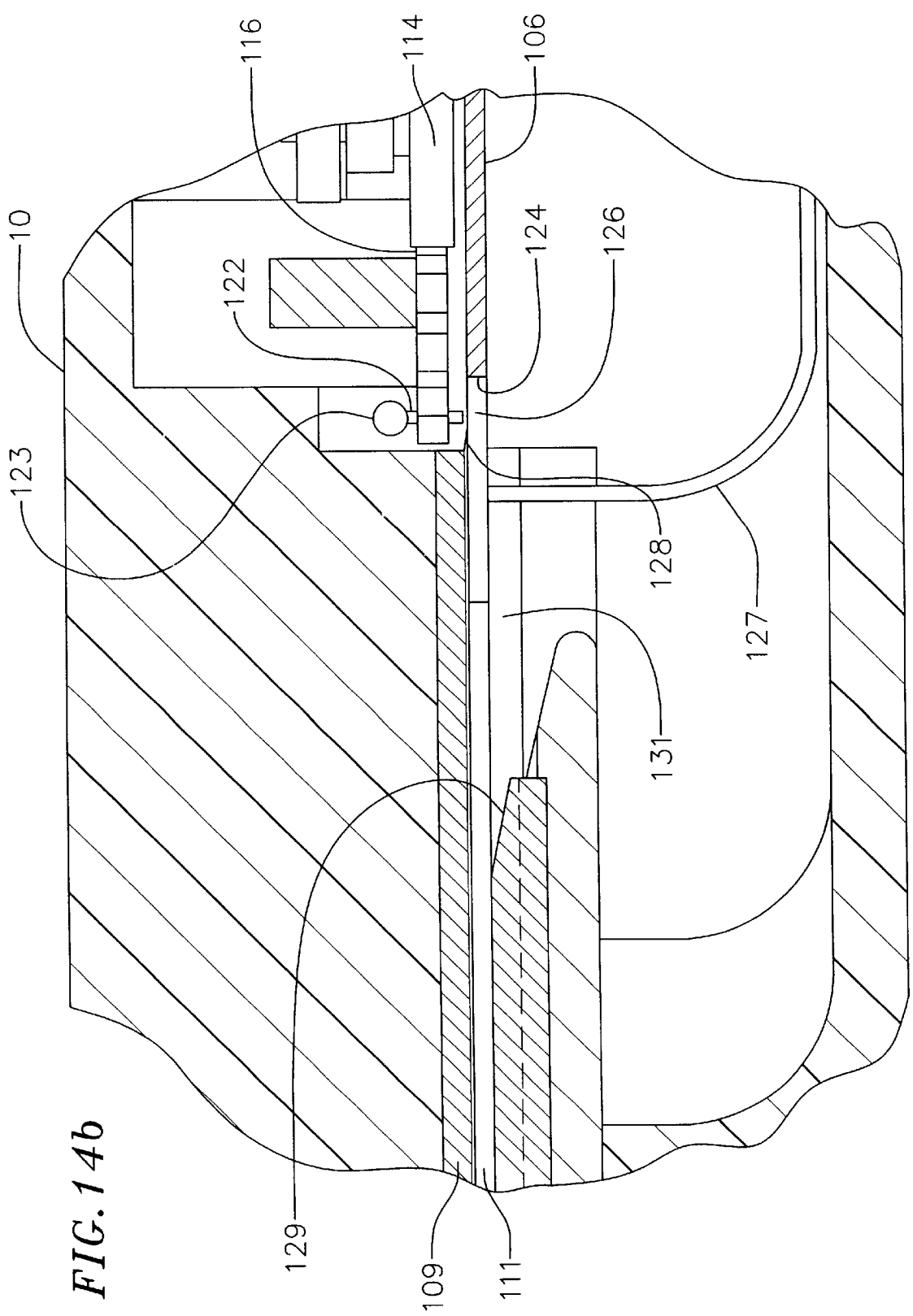
Figure 14C:
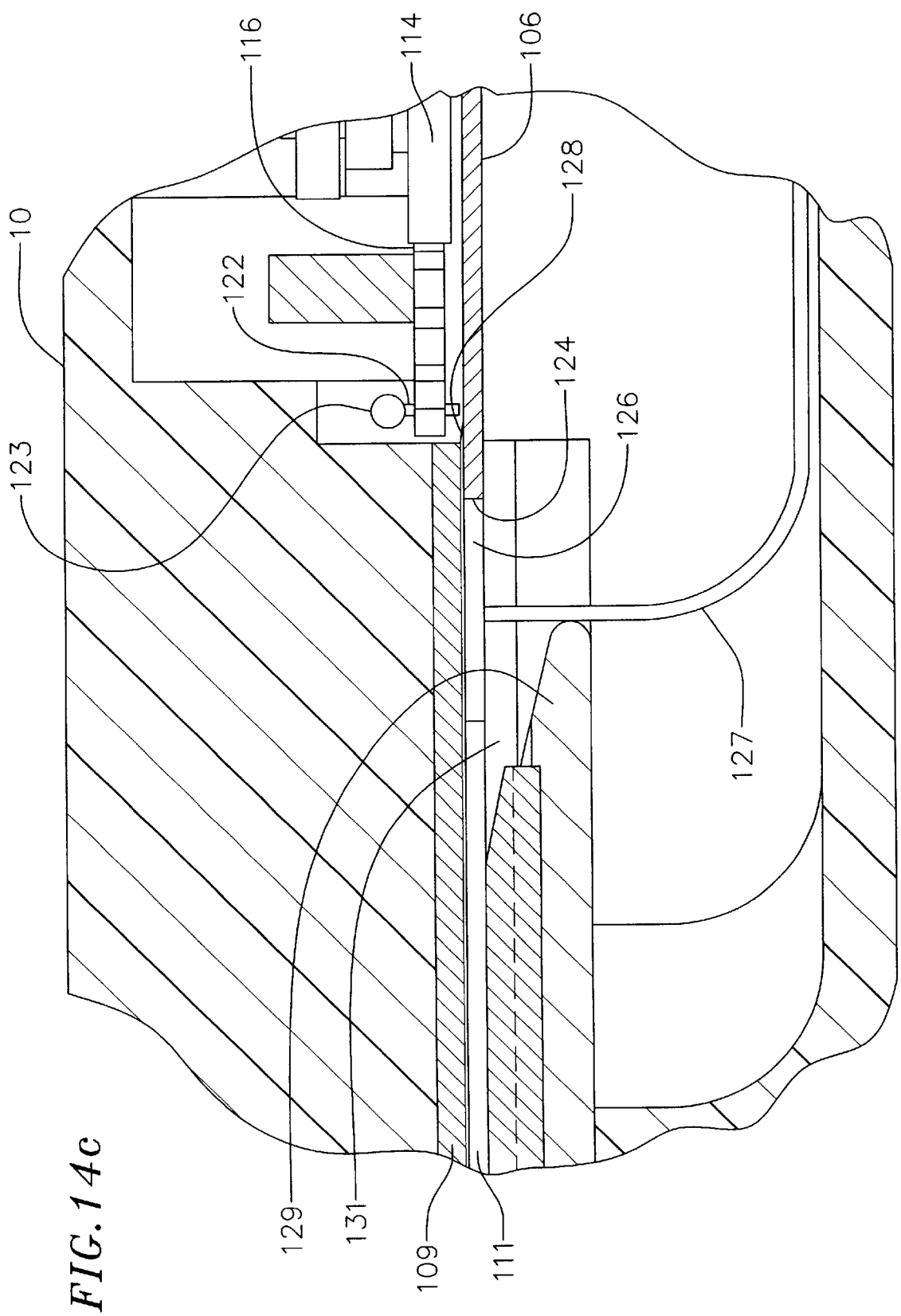
Figure 14D:
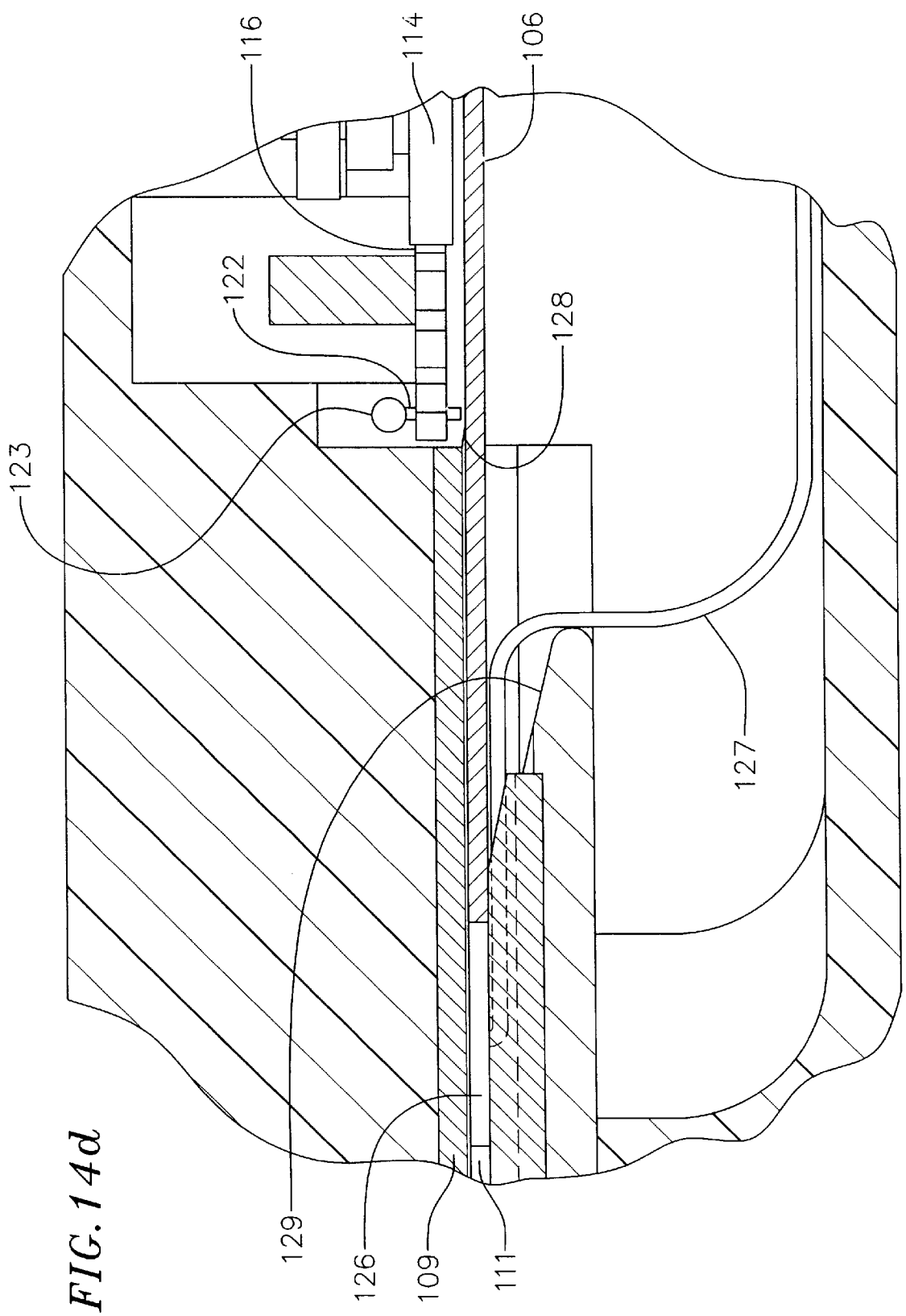

The sequence of the T-bar suture feeding into and ejection from the longitudinal bore is further illustrated by reference to FIGS. 14a through 14d. In the unactivated position of handpiece 100, wire push-rod 106 is retracted sufficiently on drum 104 to permit the distal tip of wire push-rod 106 to engage the proximal tip 124 of T-bar portion 126. As can be seen in FIG. 14(a), the T-bar portion 126 is detachably connected to suture spline 123 by spline mount tab 122. Suture strand 127 initially extends laterally from T-bar portion in a direction opposite from spline mount tab 122 and then trails proximally within the housing. FIG. 14(b) illustrates the T-bar portion 126 sufficiently displaced in longitudinal bore 111 such that spline mount tab 122 has been cut by knife 128, severing a T-bar suture from suture spline 123. In FIG. 14(c), wire push-rod has further advanced through the longitudinal bore and the trailing suture portion 127 is shown encountering guide flange 129 to guide the suture strand into keyway slot 131 which is part of longitudinal bore 111. Keyway slot 131 permits the suture strand portion to trail the T-bar portion of the suture without becoming bound. This is more clearly shown in FIG. 14(d). Continued compression of the handpiece to its first limit position will eject the T-bar portion and part of the strand portion out of the distal tip of the needle. The needle is then withdrawn through the tissue which allows the remainder of the suture strand to pass through the radial distal opening of the needle. Since the handpiece is biased by torsion spring 132 to return to the unactivated position, a release of compression on the handpiece coupled with movement of the handpiece in the direction of the unactivated position will cause the wire push-rod to retract as drive rack 101 changes the direction of rotation of pinion 102. When wire push-rod 106 has been retracted sufficiently, rocker arm 113 will be urged to rotate clockwise by spring arm 118 thereby causing gear advance pawl 121 to index the ratchet mechanism and advance the suture spline 123 to feed the next T-bar suture.

This invention is not to be limited by the embodiment shown in the drawings and described in the description which is given by way of example and not of limitation, but only in accordance with the scope of the appended claims.

What is claimed is:

1. A laparascopic incision closure device comprising:

a housing;

a needle having a longitudinal axis, a proximal and distal end, and an axially extending longitudinal bore therethrough where said needle has a radial distal opening in said distal end and a radial proximal opening in said proximal end and where said longitudinal bore communicates only with said radial distal opening and said radial proximal opening forming a continuously bounded passageway, and where said needle is attached to said housing at said proximal end;

a plurality of T-bar sutures where each said T-bar suture comprises a T-bar portion and a suture portion integrally connected, and where said suture portion is so adapted and disposed in said housing and said longitudinal bore so as to permit axial passage of said T-bar portion and said suture portion through said longitudinal bore, and where said plurality of T-bar sutures are stored in said housing and said longitudinal bore;

ejection means for sequentially ejecting said T-bar portion and said suture portion through said radial distal opening and through tissue adjacent to an incision;

whereby a Laparascopic incision can be quickly and efficiently closed by sequential placement of a T-bar suture on opposite sides of said incision and then tying said respective suture portions to close the wound.

2. The device according to claim 1 in which said ejection means comprises a plunger mechanism for advancing said T-bar portion and said suture portion axially within said longitudinal bore and for ejecting a single T-bar suture out of said radial distal opening, and trigger means for releasing said plunger mechanism whereby a T-bar portion and suture portion of a T-bar suture is ejected from said longitudinal bore.

3. The device according to claim 2 wherein said plunger mechanism comprises a plunger coaxial with said longitudinal bore having an end engaging a T-bar suture loaded in said longitudinal bore, a plunger shaft attached to said plunger and slidably mounted in said housing; and operating means for moving said plunger shaft and plunger forward or backward in said housing.

4. The device according to claim 1 further comprising:
  (a) a spline member having an axis of elongation movably carried by said housing where each of said plurality of T-bar portions are axially spaced and detachably carried by said spline member, and;
  (b) ratchet means responsive to said ejection means for sequentially advancing said spline member axially so as to feed one of said T-bar portions into said longitudinal bore.

5. The device according to claim 4 in which said ejection means comprises a plunger mechanism for advancing one of said T-bar portions and said suture portions respectively axially within said longitudinal bore and for ejecting said T-bar portion through said radial distal opening, and trigger means for activating said plunger mechanism whereby a T-bar portion and suture portion of a T-bar suture may be ejected from said longitudinal bore.

6. The device according to claim 5 wherein said plunger mechanism comprises a flexible push-rod bi-axially movable in said longitudinal bore having a first and second end and a carriage member responsive to said trigger means where said second end is so adapted to said carriage member to permit said flexible push-rod to move bi-axially in said longitudinal bore.

7. The device according to claim 4 where said T-bar portion is made of an absorbable material.

8. The device according to claim 1 where said T-bar portion is made of an absorbable material.

9. A laparascopic incision closure device comprising:
  (a) a housing;
  (b) a needle having a longitudinal axis, a proximal and distal end, and an axially extending longitudinal bore therethrough where said needle, has a radial distal opening and a radial proximal opening and where said longitudinal bore only communicates only with said distal and proximal opening forming a continuously bounded passageway, and where said needle is carried by said housing;
  (c) a spline member having an axis of elongation carried by said housing;
  (d) a plurality of axially spaced T-bar sutures detachably carried by said spline member where each said T-bar suture comprises a T-bar portion and a suture portion integrally connected, and where each said T-bar suture is so dimensioned and proportioned to permit axial passage of said T-bar portion and said suture portion through said longitudinal bore;
  (e) ratchet means for sequentially advancing said spline member axially so as to feed one of said T-bar portions into said longitudinal bore;
  (f) ejection means for detaching said T-bar suture from said spline member and for advancing said T-bar portion and said suture portion within said longitudinal bore and ejecting said T-bar portion through said radial distal opening.

10. The device according to claim 9 wherein said ejection means comprises a flexible push-rod and rotatable carriage where said flexible push-rod is so carried by said rotatable carriage that upon sufficient rotation of said rotatable carriage said T-bar portion and said suture portion are axially advanced within said longitudinal bore and said T-bar portion ejected out of said radial distal opening.

11. The device according to claim 10 wherein said ejection means further comprises trigger means comprising a handpiece so carried by said housing to permit bi-directional movement of said handpiece relative to said housing, a spring member in biased relationship with said handpiece, a rack and pinion responsive to bi-directional movement of said handpiece for rotating said rotatable carriage, and a rocker arm responsive to bi-directional movement of said handpiece for activating said ratchet means.

12. The device according to claim 9 where said T-bar portion is made of an absorbable material.

* * * * *